(12) United States Patent
Sanders et al.

(10) Patent No.: US 7,892,264 B2
(45) Date of Patent: Feb. 22, 2011

(54) FIXATION DEVICE FOR THE TALUS

(75) Inventors: Roy Sanders, Tampa, FL (US); Priya Prasad, Warsaw, IN (US); Chris Bremer, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1122 days.

(21) Appl. No.: 11/095,947

(22) Filed: Mar. 31, 2005

(65) Prior Publication Data

US 2006/0235396 A1    Oct. 19, 2006

(51) Int. Cl.
*A61B 17/80* (2006.01)
(52) U.S. Cl. .................................................. 606/280
(58) Field of Classification Search ................. 606/69, 606/70, 71
See application file for complete search history.

(56) References Cited

U.S. PATENT DOCUMENTS

| | | | | |
|---|---|---|---|---|
| 1,704,883 | A * | 3/1929 | Cullinan | 296/9 |
| 4,762,122 | A * | 8/1988 | Slocum | 606/70 |
| 4,800,874 | A * | 1/1989 | David et al. | 606/69 |
| 4,903,691 | A | 2/1990 | Heinl | |
| 5,904,684 | A * | 5/1999 | Rooks | 606/69 |
| 6,197,028 | B1 * | 3/2001 | Ray et al. | 606/61 |
| 6,206,883 | B1 | 3/2001 | Tunc | |
| 6,692,498 | B1 * | 2/2004 | Niiranen et al. | 606/69 |
| 2001/0012940 | A1 * | 8/2001 | Tunc | 606/76 |
| 2002/0128654 | A1 * | 9/2002 | Steger et al. | 606/69 |

(Continued)

FOREIGN PATENT DOCUMENTS

WO    WO 2004/032751    4/2004

OTHER PUBLICATIONS

"Foot and Ankle Conditions—Fractures of the Talus," http://www.drmyerson.com/conditions/trauma/fractures_talus.html, Mar. 22, 2005, 7 pages.

(Continued)

*Primary Examiner*—Thomas C Barrett
*Assistant Examiner*—Nicholas Woodall
(74) *Attorney, Agent, or Firm*—Maginot, Moore & Beck

(57) ABSTRACT

A fixation device for reduction and fixation of fractures of the talus bone of the foot includes a thin titanium alloy plate having a lower wing configured for attachment to the lateral aspect of the talus and an upper wing configured for attachment to the dorsal aspect of the talus. The plate includes a substantially perpendicular or right angle bend between the lower and upper wings. In one embodiment, each wing includes three screw holes arranged in a generally triangular pattern. Two holes on each plate are situated in tabs and the center of the plate has a reduced width so that the plate presents a minimal profile. One of the tabs on the upper wing is bent away from the lower wing at a pre-determined angle so that the wing conforms to the shape of the talus. In an alternative embodiment, the upper wing includes a step portion between the lower wing and the bent tab and carrying one screw hole. In this embodiment, the bent tab is generally elongated with one or two screw holes disposed along its length.

17 Claims, 4 Drawing Sheets

U.S. PATENT DOCUMENTS

2003/0060827 A1* 3/2003 Coughln ................. 606/70
2003/0088252 A1* 5/2003 Kaikkonen et al. ........... 606/76
2004/0044345 A1* 3/2004 DeMoss et al. ............. 606/73
2006/0089648 A1* 4/2006 Masini .................. 606/69

OTHER PUBLICATIONS

"Talus Fractures," unknown date, 2 pages.
"Operative Treatment for Talar Neck Frx:," http:/www.wheelesonline.com/oo3/2180.htm, Mar. 22, 2005, 2 pages.

* cited by examiner

FIXATION DEVICE FOR THE TALUS

The present invention relates to fixation devices for the bones of the foot, and particularly for the talus bone. The invention is especially suitable for reducing fractures of the neck of the talus.

The talus is a critical bone of the ankle joint. As shown in FIGS. 1-2, the talus connects the leg to the foot. In particular, the tibia articulates on talar dome (see FIG. 6) to produce the multiple degrees of freedom of movement of the ankle, including the upward and downward movement (dorsiflexion and plantarflexion). The talus also articulates on the calcaneous bone to produce the majority of the inward and outward movement (inversion and eversion) of the foot.

Fractures of the talus typically involve either the talar neck or lateral process, or osteochondral fractures of the talar dome. Talar neck fractures are usually high-energy injuries involving hyperdorsiflexion of the ankle. Such injuries often occur in a motor vehicle accident in which the ankle is hyperflexed by the brake pedal. On rare occasions, talar neck fractures involve displacement of the bone fragments, which are significant medical emergencies because of the risk of avascular necrosis for a talus bone with already limited vascularization.

Fractures of the talus can be extremely significant, and even with good treatment can lead to numerous complications. Some complications are as a result of joint deformity once the talus has healed, some occurring from damage to the blood supply for the bone, and others from arthritis. In some cases, a main fracture of the talus will be accompanied by additional smaller fractures on the inside of the bone. When the main fracture is fixed it is often difficult to reposition the bone correctly so that the foot is turned inward (a varus deformity). The only reliable way to correct this deformity has been a triple arthrodesis in which the three joints at the back of the foot involving the talus are fused.

Many deformity related complications can be avoided at the initial surgical treatment with optimum reduction and fixation of the talar fracture. In the most common approach, a pair of bone screws are placed posterolateral to anteromedial, or perpendicular to the fracture line (for the typical talar neck fracture). Anteromedial screw placement is used for some fractures, such as those involving medial side comminution, and is often accompanied by a medial osteotomy.

Reduction and fixation of talar fractures has been limited to bone screws and pins. This surgical approach is acceptable for relatively minor fractures. Where the talar fracture involves comminution, the success of the procedure depends upon the surgeon's ability to piece the fragments together, restore them to their proper anatomic position, and immobilize the bone until fusion occurs. For fractures with only minimal or no comminution, a combination of screws and pins may be acceptable for a successful treatment. However, where more severely comminuted fractures are involved, fixation and reduction using screws and pins is usually insufficient.

What is needed is a fixation device for the talus that is especially adapted for that bone of the foot. The need is especially great for a fixation device that is well-suited to reduce and fix a wide range of types of talar fractures, including highly comminuted fractures.

SUMMARY OF THE INVENTION

In view of these needs, the present invention provides a talar fixation device in the form of a low-profile plate configured for attachment to that talar. The plate is specifically configured for attachment across the lateral and dorsal aspects of the talus, particularly spanning the talar neck.

The plate includes a lower wing configured for attachment to the lateral aspect of the talus and an upper wing configured for attachment to the dorsal aspect of the talus. The plate includes a first bend region between the lower and upper wings that is configured so that the lower and upper wings can be simultaneously in substantially uniform contact with the talus. In the preferred embodiment, the first bend region defines a substantially perpendicular angle between the two wings.

The plate further defines a plurality of holes in each of the lower wing and upper wing. Each of the holes is preferably configured to receive a bone engaging fastener therethrough, such as a bone screw configured for attachment of the plate to the talus. In the preferred embodiment, the screw holes are identically configured and are adapted to receive differently sized bone screws.

In one aspect of the invention, the upper wing includes a second bend region in which a bent portion of the plate carrying one of the plurality of holes is bent away from the lower wing. In the preferred embodiment, the second bend region defines an angle between the bent portion of the plate and a plane defined through the upper wing that is about seventy degrees (70°). This second bend region allows the upper wing to conform to the contour of the dorsal aspect of the talus. The bent portion also positions a bone screw for reduction and fixation of the talus at a different orientation than the bone screws passing through the remainder of the upper wing and through the lower wing.

In a flat configuration, the lower and upper wings of the plate are substantially symmetric about a transverse centerline through the plate. When the plate is bent at the first bend region, the lower wing has a length from the bend that is greater than the length of the upper wing from the bend.

In one feature of the device, the perimeter of the plate is configured to reduce the prominence of profile of the plate. Thus, in one feature, the first bend region has a width that is less than the greatest width of either wing. In other words, the plate necks down from each wing to the central bend region. The plate in a flat configuration resembles a bow-tie or butterfly shape.

In another feature, each of the wings defines a pair of tabs, each carrying one of the plurality of screw holes. One of the tabs on the upper wing includes the bent portion. In a preferred embodiment, each wing includes three screw holes, one in each tab and one inboard and centrally located between the tabs. In certain embodiments, the three holes in each of the wings are arranged in a generally triangular pattern.

In a further preferred embodiment of the invention, a talus fixation device includes a plate that includes a lower wing configured for attachment to the lateral aspect of the talus, and an upper wing configured for attachment to the dorsal aspect of the talus. The lower wing includes a pair of holes for receiving bone fasteners for medial entry into the talus. The upper wing includes a step portion that is connected to the lower wing by a first bend portion. The first bend portion is configured so that the step portion sits on the dorsal aspect of the talus when the lower wing is substantially flush with the lateral aspect of the bone.

The step portion also defines a screw hole to receive a bone screw or similar fastener. The step portion blends into a second bend portion to support a bent tab. The bent tab carries two screw holes in one embodiment or a single screw hole in an alternative embodiment. The bent tab is configured to engage the anterior face of the talar dome so that the fixation device provides for attachment to talus in multiple degrees of freedom.

It is one object of the invention to provide a fixation device that is adapted to the talus bone of the foot. One important benefit of the device of the present invention is that it permits reduction and fixation of a wide variety of fractures of the talus, including severely comminuted fractures. Another benefit of the device is that is provides for screw fixation of the talus at multiple orientations.

A further benefit is that the configuration of the device helps "cup" or retain bone fragments to ensure proper reconstruction of the fractured talus. Other objects and benefits of the invention will become apparent upon consideration of the following written description taken together with the accompanying figures.

DESCRIPTION OF THE PREFERRED EMBODIMENTS

Figure 1:
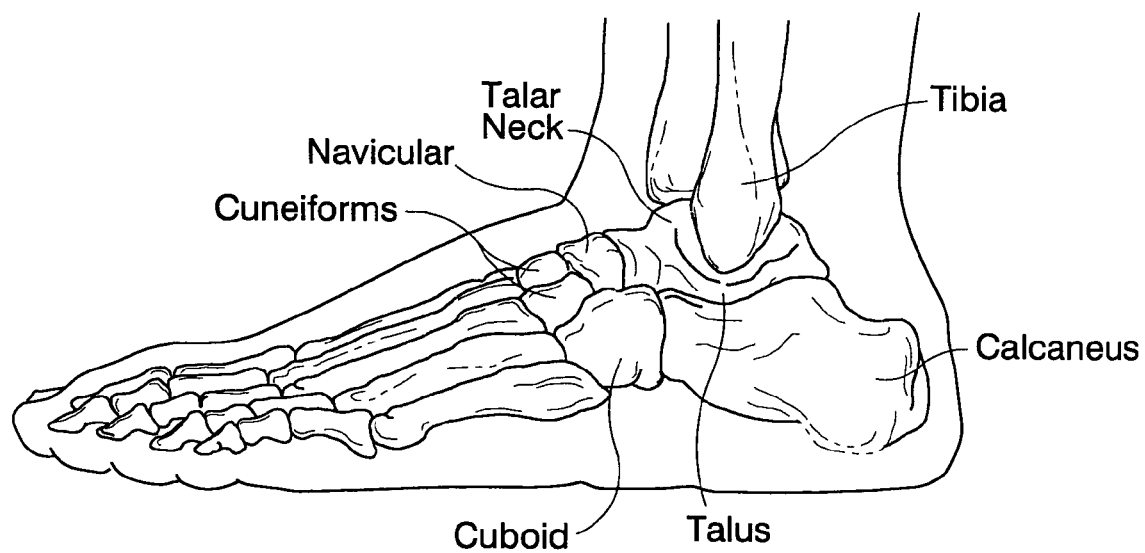
FIGS. 1-2 are lateral and anterior views of the bones of the foot with particular emphasis on the talus bone.
Figure 2:
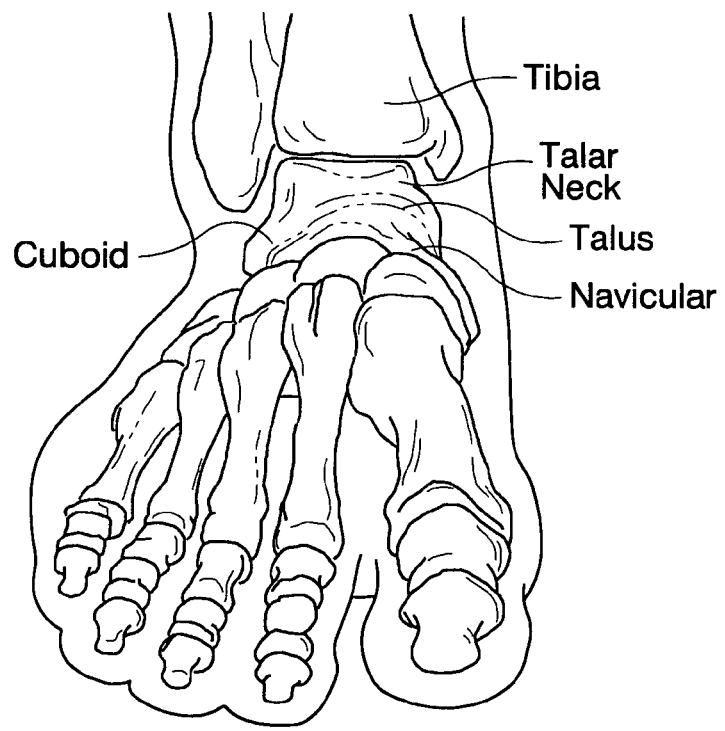

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3:
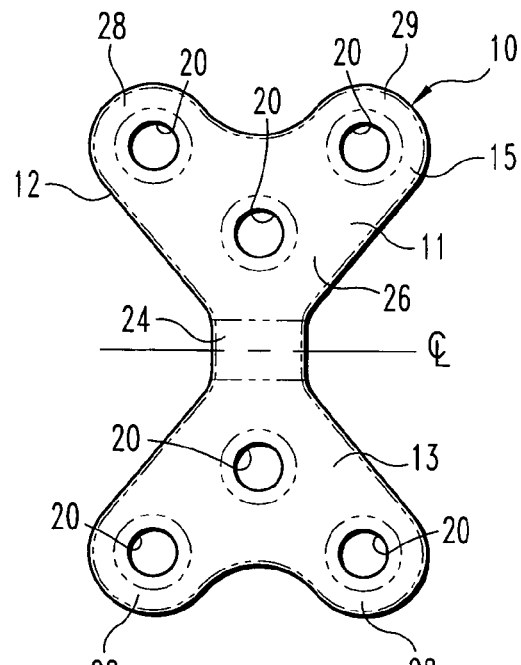
FIG. 3 is a plan view of a fixation device for the talus in accordance with one embodiment of the invention.

The present invention provides a fixation device 10 that is initially configured as a flat plate 11, as shown in FIG. 3. The plate has a minimal thickness, about 1.0 mm or less, to reduce the prominence of the plate above the talus. In the preferred embodiment, the plate is formed of a medical grade metal, such as a titanium alloy. Most preferably, the plate 11 is formed of the titanium alloy TI-6AL-4V.

The plate 11 includes an lower wing 13 and an upper wing 15 that are substantially symmetrical about the centerline CL of the plate. Each wing defines a plurality of holes 20 configured to receive a bone engaging fastener therethrough. More particularly, the holes 20 are configured to receive known bone screws for fixation of the bones of the foot. The screws may be cannulated or non-cannulated, locking or non-locking, and fully or partially threaded screws. In the preferred embodiment of the invention, the holes are configured to accept 2.7 mm or 3.5 mm screws that are sized for fixation within the talus bone.

Figure 4:
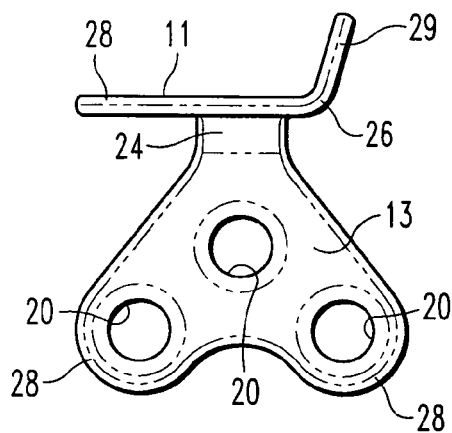
FIG. 4 is a lateral view of the fixation device shown in FIG. 3 in which the device is configured for attachment to the talus.
Figure 5:
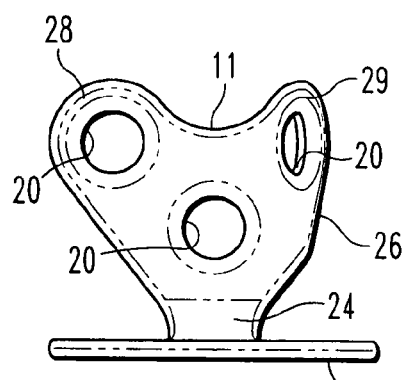
FIG. 5 is a dorsal view of the fixation device shown in FIG. 4.
Figure 6:
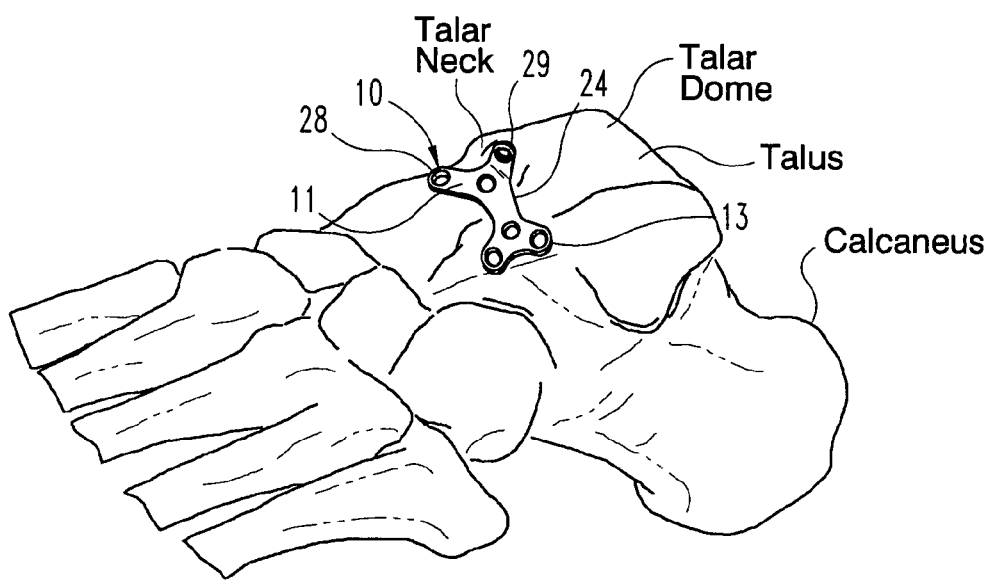
FIG. 6 is a perspective view of the dorsal aspect of the foot with the fixation device shown in FIGS. 4-5 mounted on the talus bone.

The plate 11 includes a first bend region 24 disposed across the centerline CL between the two wings 13, 15. As shown in FIGS. 4-5, the plate is bent at substantially a right angle. In this configuration, the lower wing 13 of the plate is in substantially uniform contact with the lateral aspect of the talus, as shown in FIG. 6, while the upper wing 15 is in substantially uniform contact with the medial aspect of the bone.

In order to minimize the plate profile, the perimeter 12 of the plate is contoured to generally follow the screw holes. Thus, in the preferred embodiment, each wing includes tabs 28, 29 which carry a corresponding one of the screw holes 20. As seen best in FIG. 3, the perimeter 12 necks down from each of the wings 13, 15 to the first bend region 24 so that each wing takes on a generally triangular, or even heart-shaped, configuration. In a specific embodiment, the bend region 24 has a width of about 5.0 mm, while the centerline of the holes 20 on each of the tabs are separated by a width of about 12.2 mm. This reduced width at the bend region 24 allows the plate to be bent prior to attachment to the bone in order to accommodate minor variations in the geometry of the talus.

Figure 7:
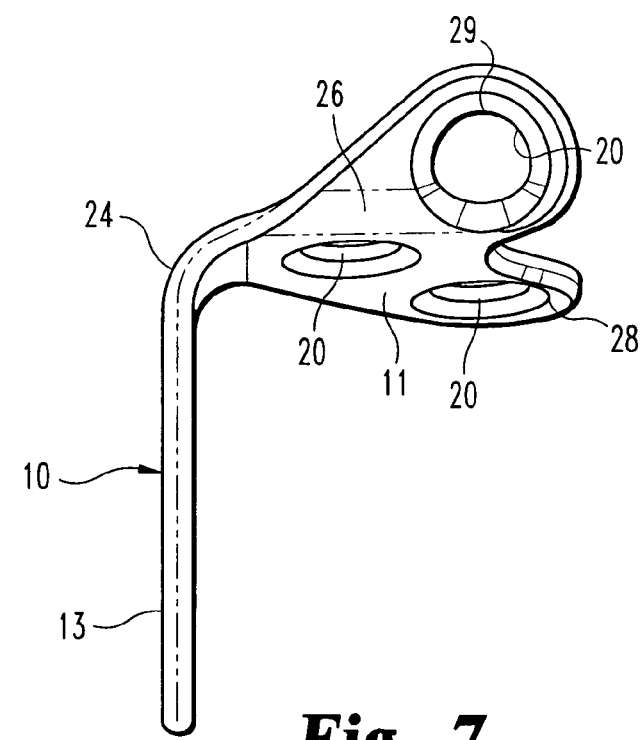
FIG. 7 is an anterior view of the fixation device shown mounted on the talus bone in FIG. 6.

The screw holes 20 in the tabs 28 of the opposing wings are separated by a length dimension of about 22.9 mm. While the bend region 24 is centrally located between the tabs, the plate may be bent offset from the centerline CL so that the lower wing 13 has a longer area of contact with the talus than the upper wing 15, as shown in FIG. 7. In a specific embodiment, the tabs 28 in the lower wing 13 position the center of the holes 20 about 12.3 mm from the bend, while the holes in the tabs 28, 29 of the upper wing 15 are located about 11.8 mm from the bend.

In the preferred embodiment, each wing includes three holes 20 arranged in a triangular pattern, as seen in FIG. 3. The holes in the tabs 28, 29 are aligned across the width of the plate, while the middle hole in the triangular pattern is offset along the length of the plate. In a specific embodiment, each middle hole is offset by about 4.8 mm from the holes in the tabs, and each is aligned along the longitudinal centerline of the plate. The screw holes all preferably have the same diameter, which is about 3.8 mm in a specific embodiment.

In a further feature of the invention, the upper wing 15 of the plate includes a second bend region 26. This bend region 26 repositions the tab 29 at an angle relative to the plate of the upper wing 15 of the plate 11. In the preferred embodiment, the tab 29 is bent upward, or away from the lower wing, at an angle of about 75 degrees from the plane of the wing. This bend allows the upper wing 15 to conform to the dorsal aspect of the talus, as shown in FIG. 6.

The present invention provides a fixation device 10 that is configured for stable attachment to the talus. The two wings 13, 15 of the plate 11 are arranged to engage the lateral and medial aspect of the talus and especially to span the neck of the bone where the majority of the talus fractures occur. The plate 11 presents multiple screw holes at two orientations that improve the surgeon's ability to reduce even severely comminuted fractures. Unlike the prior technique of introducing two bone screws or pins along substantially the same line through the bone, the plate 11 of the present invention allows lateral to medial and dorsal to plantar placement of screws or pins. The minimal thickness of the plate allows the plate to more closely conform to the talus when the plate is attached to the bone. The combination of the angled plate 11 and the multiple screw placements in different orientations provides a sold fixation of the reduced bone fragments. The lower and upper wings 13, 15 act to "cup" the bone fragments when the screws are tightened to reduce the fracture(s).

Figure 8:
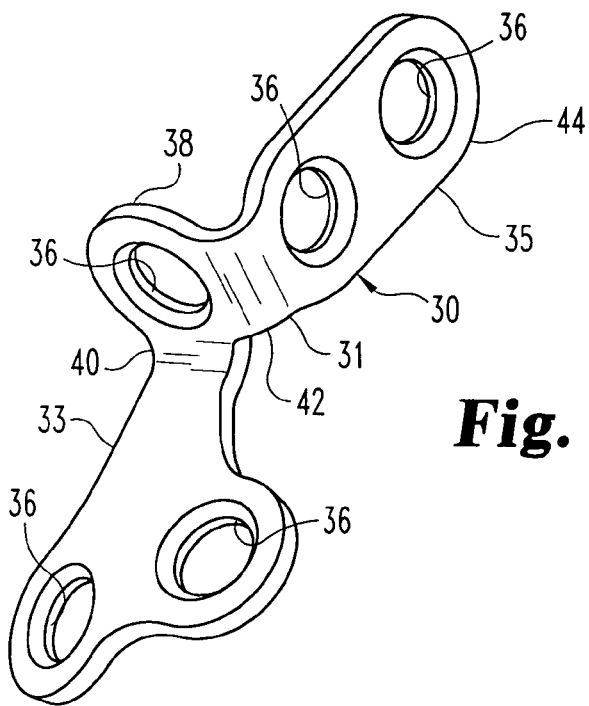
FIG. 8 is a perspective view of an alternative embodiment of the fixation device for the talus shown from the vantage point of the bone engaging surfaces.
Figure 9:
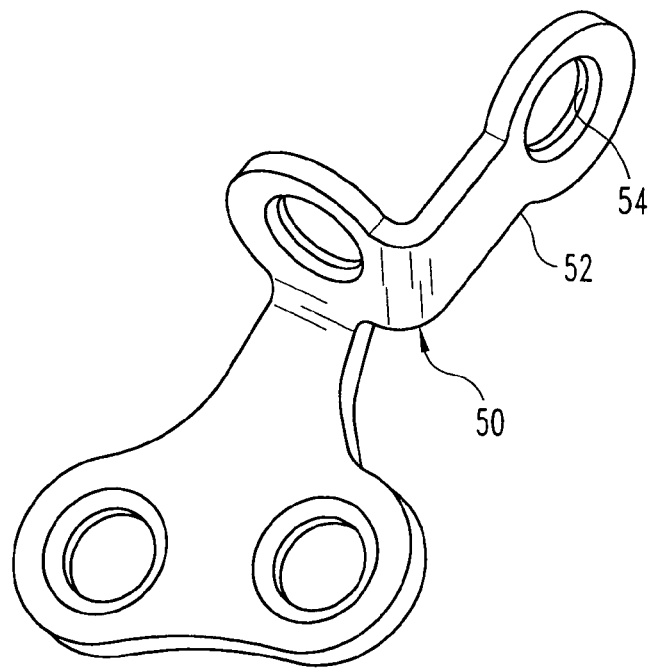
FIG. 9 is a perspective view of a modification of the alternative embodiment shown in FIG. 23.

In a further preferred embodiment, the geometry of the talus fixation devices 30 and 50 are modified from the previous embodiments, as depicted in FIGS. 8-9. The device 30 includes a plate 31 that includes a lower wing 33 configured for attachment to the lateral aspect of the talus, and an upper wing 35 configured for attachment to the dorsal aspect of the talus. The lower wing 33 includes a pair of holes 36 for receiving bone fasteners, such as the bone screws discussed above.

The upper wing 35 includes a step portion 38 that is connected to the lower wing 33 by a first bend portion 40. The first bend portion 40 is configured so that the step portion 38 sits on the dorsal aspect of the talus when the lower wing is substantially flush with the lateral aspect of the bone. The step portion 38 also defines a screw hole 36 to receive a bone screw or similar fastener. The step portion 38 blends into a second bend portion 42 to support a bent tab 44. The bent tab 44 carries two screw holes 36, as shown in FIG. 8. The screw holes are preferably aligned along a longitudinal axis of the bent tab, or along an axis projecting upward from the dorsal surface of the talus. In an alternative embodiment, the fixation device 50 shown in FIG. 9 is similar to the device 30, except that the bent tab 52 includes only a single screw hole 54, as opposed to the two screw holes shown in FIG. 8. The bent tab 44 is configured to engage the anterior face of the talar dome in substantially the same manner as the bent tab 29 of the device 10 shown in FIGS. 6-7. The selection of the one-hole or two-hole version of the bent tab depends upon the size of the anterior face of the talar dome. In some cases, the dorsal surface of the talus and the anterior surface of the talar dome may be prepared to accommodate the upper wings of the devices 30, 50.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For example, the configurations of the devices 10, 30 and 50 shown in FIGS. 3-5 and 8-9 are for right foot, while the configuration shown in FIGS. 6-7 is for fixation to the left foot.

What is claimed is:

1. A fixation device for fixation of fractures of the talus bone of the foot comprising:
    a plate having a lower wing configured for attachment to the lateral aspect of the talus and an upper wing configured for attachment to the dorsal aspect of the talus;
    said plate including a first bend region between said lower and upper wings configured so that said upper wing is oriented at an angle relative to said lower wing so that said lower and upper wings can be simultaneously in substantially uniform contact with the talus;
    said plate further defining a plurality of holes in each of said lower wing and upper wing, each of said holes configured to receive a bone engaging fastener therethrough for attachment of said plate to the talus; and
    said upper wing including a second bend region in which a bent portion of said plate carrying at least one of said plurality of holes is bent away from said lower wing,
    wherein said first bend region has a width that is less than the largest width of either of said wings,
    wherein said upper wing includes a step portion between said first bend region and said second bend region, said step portion including at least one of said plurality of holes, and
    wherein said first bend region and said second bend region are on adjacent sides of the step portion.

2. The fixation device of claim 1, wherein said first bend region forms substantially a perpendicular angle between said lower and upper wings.

3. The fixation device of claim 1, wherein said second bend region defines an angle between said bent portion of said plate and a plane defined through said upper wing that is about seventy degrees (70°).

4. The fixation device of claim 1, wherein said holes are configured to receive 2.7 mm or 3.5 mm bone screws.

5. The fixation device of claim 1, wherein said plate has a thickness of about 1.0 mm or less.

6. A bone plate for fixation of fractures of the talus bone of the foot comprising:
    a lower wing with a bone contacting surface extending along a first plane and a plurality of holes, each of the plurality of holes configured to receive a bone engaging fastener therethrough;
    a step portion with a bone contacting surface extending along a second plane and at least one hole configured to receive a bone engaging fastener therethrough;
    a first bend region between the lower wing and the step portion and configured so that the bone contacting surface of the step portion and the bone contacting surface of the step portion form an angle;
    an upper wing portion with a bone contacting surface extending along a third plane and at least one hole configured to receive a bone engaging fastener therethrough; and
    a second bend region defining a bend axis between the step portion and the upper wing and configured so that the bone contacting surface of the step portion and the bone contacting surface of the upper wing form an obtuse angle,
    wherein the intersection of the first plane and the third plane defines a line that intersects the bend axis.

7. The bone plate of claim 6, wherein the at least one hole of the upper wing portion comprises two holes.

8. The bone plate of claim 6, wherein the angle is about 90 degrees.

9. The bone plate of claim 6, wherein the obtuse angle is about two-hundred and fifty degrees (250°).

10. The bone plate of claim 6, wherein the plurality of holes are configured to receive 2.7 mm or 3.5 mm bone screws.

11. The bone plate of claim 6, wherein the plate has a thickness of about 1.0 mm or less.

12. The bone plate of claim 6, wherein the first bend region has a width that is less than the largest width of the upper wing and less than the largest width of the lower wing.

13. A bone plate for fixation of fractures of the talus bone of the foot comprising:
    a lower wing with a bone contacting surface extending along a first plane and a plurality of holes configured to receive a bone engaging fastener therethrough;
    a step portion with a bone contacting surface extending along a second plane which intersects the first plane and at least one hole configured to receive a bone engaging fastener therethrough;
    an upper wing portion with a bone contacting surface extending along a third plane which intersects the second plane and at least one hole configured to receive a bone engaging fastener therethrough;

wherein the intersection of the first plane and the second plane defines a first bend axis and the intersection of the second plane and the third plane defines a second bend axis which intersects the first bend axis.

14. The bone plate of claim 13, wherein the at least one hole of the upper wing portion comprises two holes.

15. The bone plate of claim 13, wherein the first plane and the second plane are substantially perpendicular.

16. The bone plate of claim 13, wherein the second plane and the third plane define an angle of about seventy degrees (70°).

17. The bone plate of claim 13, wherein the first bend axis lies within a bend region with a width that is less than the largest width of the upper wing and less than the largest width of the lower wing.

\* \* \* \* \*

UNITED STATES PATENT AND TRADEMARK OFFICE
CERTIFICATE OF CORRECTION

| | | |
|---|---|---|
| PATENT NO. | : 7,892,264 B2 | Page 1 of 1 |
| APPLICATION NO. | : 11/095947 | |
| DATED | : February 22, 2011 | |
| INVENTOR(S) | : Sanders et al. | |

It is certified that error appears in the above-identified patent and that said Letters Patent is hereby corrected as shown below:

| <u>Col.</u> | <u>Line</u> | |
|---|---|---|
| Title Page, Item [57] | 12 | Delete "pre-determined" and insert --predetermined--. |

In the Specification

| | | |
|---|---|---|
| 3 | 9 | Delete "that is provides" and insert --that it provides--. |
| 3 | 60 | Delete "an lower" and insert --a lower--. |
| 4 | 67 | Delete "sold fixation" and insert --solid fixation--. |

In the Claims

| | | |
|---|---|---|
| 6 Claim 6 | 28-30 | Delete First occurrence of "the bone contacting surface of the step portion" and insert --the bone contacting surface of the lower wing--. |

Signed and Sealed this
Twenty-eighth Day of October, 2014

Michelle K. Lee
*Deputy Director of the United States Patent and Trademark Office*